United States Patent
Ni et al.

(10) Patent No.: US 10,835,617 B2
(45) Date of Patent: Nov. 17, 2020

(54) VEGF ANTIBODY-DRUG CONJUGATES

(71) Applicants: Jinsong Ni, Irvine, CA (US); Rong Yang, Mission Viejo, CA (US)

(72) Inventors: Jinsong Ni, Irvine, CA (US); Rong Yang, Mission Viejo, CA (US)

(73) Assignee: ADS THERAPEUTICS LLC, Reno, NV (US)

( * ) Notice: Subject to any disclaimer, the term of this patent is extended or adjusted under 35 U.S.C. 154(b) by 51 days.

(21) Appl. No.: 16/072,415

(22) PCT Filed: Feb. 2, 2017

(86) PCT No.: PCT/US2017/016107
§ 371 (c)(1),
(2) Date: Jul. 24, 2018

(87) PCT Pub. No.: WO2017/136486
PCT Pub. Date: Aug. 10, 2017

(65) Prior Publication Data
US 2019/0030179 A1     Jan. 31, 2019

Related U.S. Application Data

(60) Provisional application No. 62/291,361, filed on Feb. 4, 2016.

(51) Int. Cl.
| | |
|---|---|
| *A61K 47/68* | (2017.01) |
| *A61K 39/395* | (2006.01) |
| *C07K 16/22* | (2006.01) |
| *A61K 9/08* | (2006.01) |
| *A61K 9/00* | (2006.01) |
| *C07K 16/00* | (2006.01) |
| *A61K 31/496* | (2006.01) |
| *A61K 47/46* | (2006.01) |

(52) U.S. Cl.
CPC ........ *A61K 47/6845* (2017.08); *A61K 9/0048* (2013.01); *A61K 9/08* (2013.01); *A61K 31/496* (2013.01); *A61K 39/3955* (2013.01); *A61K 47/6803* (2017.08); *A61K 47/6849* (2017.08); *C07K 16/00* (2013.01); *C07K 16/22* (2013.01); *A61K 47/46* (2013.01); *C07K 2317/24* (2013.01)

(58) Field of Classification Search
None
See application file for complete search history.

(56) References Cited

U.S. PATENT DOCUMENTS

| | | |
|---|---|---|
| 2006/0088530 A1 | 4/2006 | Chen |
| 2014/0030273 A1 | 1/2014 | Verploegen et al. |
| 2015/0320879 A1 | 11/2015 | Lyon et al. |
| 2015/0337042 A1 | 11/2015 | Reilly et al. |
| 2015/0376271 A1 | 12/2015 | Perlroth et al. |

FOREIGN PATENT DOCUMENTS

| | | |
|---|---|---|
| WO | 2012068030 A1 | 5/2012 |
| WO | 2014055913 A1 | 4/2014 |

OTHER PUBLICATIONS

Borisey et al. (2003). PNAS. 100(13):7977-7982.*

* cited by examiner

*Primary Examiner* — Christine J Saoud
*Assistant Examiner* — Jon M Lockard
(74) *Attorney, Agent, or Firm* — SZDC Law P.C.

(57) ABSTRACT

A method of producing synergistic and enhanced efficacy in treating a disease in a subject includes providing an antibody, the antibody being a classic antibody or a modified biologic molecule that blocks a first target in the subject; providing a drug, the drug being a small molecule agent that blocks the first target or a second target in the subject; connecting the antibody and the drug with a linker to form an Antibody-Drug Synergism (ADS) compound; and treating the disease with the ADS compound. The linker is hydrolyzed in the subject over a certain time so that both the antibody and the drug exert their functions simultaneously, and the ADS compound confers better efficacy than either the antibody or the drug alone due to a synergism of the ADS compound.

4 Claims, 1 Drawing Sheet

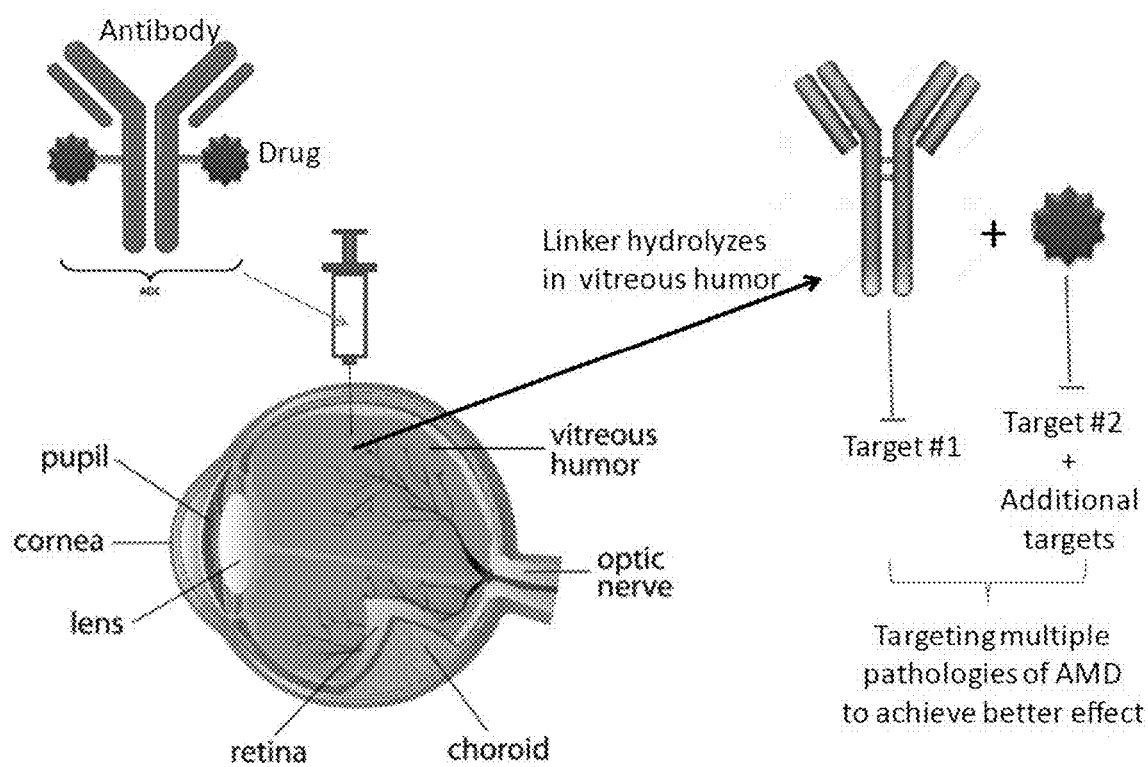
Mechanism of how ADS can be used to treat an exemplary ocular neovascular disease wet AMD.

VEGF ANTIBODY-DRUG CONJUGATES

The present invention is the national stage application of PCT/US2017/016107, filed on Feb. 2, 2017, which claims the benefit of U.S. Provisional Application No. 62/291,361, filed on Feb. 4, 2016, which is incorporated by reference for all purposes as if fully set forth herein.

BACKGROUND OF THE INVENTION

Field of the Invention

The present invention relates to an Antibody-Drug Synergism (ADS) compound for treating diseases and a method of using the same.

Discussion of the Related Art

Anti-angiogenesis strategies are effective treatments for ocular neovascular diseases such as exudative AMD (also known as wet AMD). Currently, several VEGF-neutralizing biologic drugs are on the market. An antibody against VEGF-A, bevacizumab (avastin), originally developed by Genetech for cancer, was initially used off-label for wet AMD. Genetech modified it and developed ranibizumab (lucentis) specifically for treating wet AMD and it was approved by FDA in 2006 (Rosenfeld et al 2006, Brown et al 2006, Martin et al 2011). These two antibody drugs are administered intravitreally about once every month. More recently, Regeneron developed a fusion protein between VEGFR2 extracellular binding domains and antibody Fc regions for the treatment of wet AMD. This drug, aflibercept, is approved by FDA in 2011. It has similar efficacy to ranibizumab but can be used less frequently (Stewart et al 2012). Despite the effectiveness of these drugs, further improvements are needed for better treatment of wet AMD. For example, targeting additional pathogenesis-related growth factors besides VEGF, longer interval between injections, the desire for neovascular regression and the need to treat ranibizumab-refractory patients are currently unmet. Several strategies of anti-VEGF/PDGF inhibition are currently being investigated in the clinic for wet AMD. These include a new biologic technology platform of Darpin to inhibit VEGF, a combination therapy of anti-VEGF Lucentis and anti-PDGF Fovista and a dual-darpin platform of one molecule targeting both VEGF and PDGF growth factors.

SUMMARY OF THE INVENTION

An advantage of the present invention is a method of producing synergistic and enhanced efficacy in treating a disease in a subject that includes: providing an antibody, the antibody being a classic antibody or a modified biologic molecule that blocks a first target in the subject; providing a drug, the drug being a small molecule agent that blocks the first target or a second target in the subject; connecting the antibody and the drug with a linker to form an Antibody-Drug Synergism (ADS) compound; and treating the disease with the ADS compound. The linker is hydrolyzed in the subject over a certain time so that both the antibody and the drug exert their functions simultaneously, and the ADS compound confers better efficacy than either the antibody or the drug alone due to a synergism of the ADS compound.

In one embodiment, the discease is an ocular disease, a dermatological disease, or a joint disease.

In another embodiment, the ocular disease is a neovascular disease involving abnormal angiogenesis and vessel leakage.

In another embodiment, the ADS compound is delivered or injected into an eye of the subject through intravitreal, intracameral, suprachoroidal, subconjunctival, subtenon, or topical ocular.

In another embodiment, the antibody blocks the activity of one or more pro-angiogenesis factors selected from the group consisting of the family members of VEGF, PDGF, and PlGF and receptors thereof In another embodiment, the antibody is bevacizumab, ranibizumab, ramucirumab, aflibercept, or conbercept.

In another embodiment, the small molecule agent is a multikinase inhibitor that inhibits one or more selected from the group consisting of the family members of VEGFR, PDGFR and FGFR, or an anti-angiogenesis inhibitor.

In another embodiment, the multikinase inhibitor is Axitinib, Cediranib, Linifanib, Motesanib, Nintedanib, Pazopanib, Ponatinib, Regorafenib, Sorafenib, Sunitinib, Tivozanib, or Vatalanib.

In another embodiment, the anti-angiogenesis inhibitor is Squalamine.

In another embodiment, the linker is hydrolyzed with a half-life of 1 to 24 hours, 1 to 28 days, or 1 to 4 months.

Another advantage of the present invention is an Antibody-Drug Synergism (ADS) compound for treating a disease in a subject that includes: an antibody, the antibody being a classic antibody or a modified biologic molecule that blocks a first target in the subject; a drug, the drug being a small molecule agent that blocks the first target or a second target in the subject; and a linker that is hydrolyzed in the subject over a certain time so that both the antibody and the drug exert their functions simultaneously. The ADS compound confers better efficacy than either the antibody or the drug alone due to a synergism of the antibody and the drug.

In one embodiment, the disease is an ocular disease, a dermatological disease, or a joint disease.

In another embodiment, the ocular disease is a neovascular disease involving abnormal angiogenesis and vessel leakage.

In another embodiment, the antibody is PEGylated.

In another embodiment, the antibody is bevacizumab, ranibizumab, ramucirumab, aflibercept, or conbercept.

In another embodiment, the small molecule agent is Axitinib, Cediranib, Linifanib, Motesanib, Nintedanib, Pazopanib, Ponatinib, Regorafenib, Sorafenib, Sunitinib, Tivozanib, Vatalanib, or Squalamine.

In another embodiment, the linker is hydrolyzed with a half-life of 1 to 24 hours, 1 to 28 days, or 1 to 4 months.

In another embodiment, the linker is an ester, a carbonate, a carbamate, an ether, an amide, an imine, a phosphate, a hydrozone bond, or a polymer small molecule conjugate.

In another embodiment, the ADS Compound is a dry powder for rehydration before use, a gel, or an implant.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows how the ADS technology can be used to treat ocular neovascular diseases such as wet AMD.

DETAILED DESCRIPTION OF THE ILLUSTRATED EMBODIMENTS

Reference will now be made in detail to embodiments of the present invention, example of which is illustrated in the accompanying drawings.

Antibody-Drug Synergism (ADS) technology is a new concept that utilizes the synergy between an antibody and a small molecule agent to treat a variety of diseases, for example, an ocular disease, a dermatological disease, or a joint disease. In this technology, an ADS compound is formed by linking a small molecule agent to an antibody drug through a linker via a covalent bond or other similar bonds. It differentiates from the oncology-focused antibody-drug conjugate (ADC) technology in three important ways: 1) The antibody in the ADS technology is used as a disease-modifying drug while the antibody in the ADC technology is merely a carrier to target the small molecule agent to cancer cells; Therefore, in ADS, antibody and small molecule have synergistic effect on the target disease while in ADC, antibody and small molecule will have no synergistic effect. 2) The linker in the disclosed method is cleaved outside of cells (for example, in vitreous humor of the eye) to release the small molecule agent while the linker in the ADC technology is cleaved inside cancer cells or not cleaved at all. 3) ADS technology also serves as a carrier to slowly break the linker to release the small molecule agent at the injection site to have prolong effect of the small molecule agent while in ADC, antibody does not serve this function. While the application focuses on ocular diseases to demonstrate the concept, the disclosed methods can be used for any diseases where local drug administration is a suitable treatment.

Ocular neovascular diseases are diseases of the eye that involve abnormal angiogenesis (blood vessel growth) and vessel leakage. Examples are exudative (wet) age-related macular degeneration (AMD), diabetic macular edema, retinal vein occlusion, diabetic retinopathy, cornea neovascularization and pterygium.

Anti-angiogenesis biologic drugs are effective treatments for ocular neovascular diseases such as wet AMD. Successful examples include bevacizumab (off-label use), ranibizumab, aflibercept, and conbercept; all of these are VEGF-A-neutralizing biologic agents (Rosenfeld et al 2006, Martin et al 2011, Stewart et al 2012). Despite the success of these biologic drugs, there are still unmet needs for better treatment of wet AMD. Anti-VEGF-A alone is insufficient to achieve neovascular regression, a desirable outcome for wet AMD. Another need is to treat patients that become refractive to deprivation of VEGF-A (Jo et al 2006). To address these unmet needs, new strategies have been tested in the clinic. For example, multi-target small molecule agents have been tested as topical formulations (Csaky et al 2015). But delivering small molecule to retina via topical route proved difficult and intravitreal formulations are also fraught with problems. Another strategy being tested in the clinic is to use new biologics to target multiple pathways or employing combination of two antibodies targeting different pathways. Non-clinical and clinical studies of wet AMD have demonstrated that inhibiting both VEGF and PDGF is more effective than blocking VEGF alone (Kudelka et al 2013). PDGF is a particularly attractive second target because of its involvement in vessel maintenance and fibrosis. Inhibiting PDGF could potentially lead to neovascular regression. The method disclosed here uses a novel way to target multiple pathogenic factors such as aforementioned VEGF and PDGF signaling pathways simultaneously.

The ADS technology can be used as a novel way to treat ocular neovascular diseases, such as wet AMD. It utilizes the synergism between an antibody and a small molecule agent to achieve better effects than either single component alone. A technology called antibody-drug conjugate (ADC) has been used in cancer therapy. That technology links a cancer drug, usually cytotoxic agents, to an antibody that directs the drug to cancer cells and confers some selectivity. Antibody used in the ADC platform merely acts as a carrier to bind to the targeted cancer cell and does not possess therapeutic effects. The ADC approach is used to improve the safety or pharmacokinetics profiles of cancer drugs (Kim et al 2015, Peters et al 2015) and the linkers in the ADC are designed to be cleaved inside cells to release the cancer drug or not to be cleaved at all. The method of the ADS platform differs from the ADC technology in three important ways. Instead of being an inactive carrier as in the ADC technology, the antibody in the ADS method is itself a therapeutic agent designed to have synergistic therapeutic effect with the small molecule agent linked to it; secondly, the linker in the disclosure is designed to be hydrolyzed in vitreous humor or other ocular tissues instead of inside cancer cells; thirdly, ADS technology also serves as a carrier to slowly break the linker to release the small molecule agent at the injection site to have prolong effect of the small molecule agent while in ADC, antibody does not serve this function. In addition to these three differences, the disclosed method is designed for ocular or other locally injected use instead of systemic cancer treatment. The ADS technology will allow modulation of multiple ocular targets to achieve synergistic therapeutic effects; in addition to being a therapeutic agent, the antibody in the disclosed method will also act as a carrier to facilitate sustained delivery of the small molecule agent to the vitreous, a task previously difficult to achieve. The antibody in the disclosed methods can be a classic antibody, an antibody hybrid fusion or any other biologic molecules that are designed to block any of the angiogenesis related targets such as VEGF, VEGFR, PDGF, PDGFR, FGF and FGFR. Examples of such biologic drugs include: bevacizumab and ranibizumab, ramucirumab, aflibercept and conbercept. In addition, any anti-angiogenesis protein drugs in clinical testing but not yet approved by FDA will also be included. Examples include anti-VEGF, -PDGF Darpins (Allergan), Sevacizumab (anti-VEGF, Jiangsu Simcere Pharmaceutical), TK001 (anti-VEGF, Jiangsu T-Mab Biopharma), Tanibirumab (anti-VEGFR2, PharmAbcine), LMG324 (anti-VEGF, Alcon/Norvatis), BCD-021 (bevacizumab biosimilar, Biocad), IMC-3G3 (anti-PDGFR, ImClone LLC), MEDI-575 (anti-PDGFR, Medimmune LLC), TRC105 (anti-endoglin antibody, NCI), Fovista (anti-PDGF, Ophthotech) and any others that inhibit VEGF, PDGF, VEGFR or PDGFR. The antibody in the disclosed methods can be mono-target or bi-target or multi-target biologics. In addition, the antibody in the disclosed methods can be PEGylated.

The small molecule agent in the disclosed methods can be a multikinase inhibitor against one or more tyrosine kinases. Examples of the tyrosine kinase inhibitors include: Canertinib, Crenolanib, Dacomitinib, Erlotinib, Gefitinib, Icotinib, Lapatinib, Lenvatinib, Linifanib, Motesanib, Neratinib, Quizartinib, Tandutinib, Tivantinib, Tivozanib, Vatalanib, Cediranib, Trametinib, Dabrafenib, Vemurafenib, Palbociclib, Amuvatinib, Dasatinib, Foretinib, Golvatinib, Imatinib, Nilotinib, Pazopanib, Crizotinib, Sunitinib, Sorafenib, Axitinib, Ponatinib, Ruxolitinib, Vandetanib, Cabozantinib, Afatinib, Ibrutinib, Nintedanib, Regorafenib, Idelalisib, Ceritinib, LY2874455, SU5402, and any others that inhibit VEGFR, PDGFR, and FGFR. In addition, the small molecule agent can other type of anti-angiogenesis inhibitor, such as Squalamine.

The linker in the disclosed methods can be any kind that can be cleaved in vitreous humor, ocular tissues and cells. Examples of potential vitreous-hydrolyzable linkers are esters, amides, carbamates, carbonates, imines, ethers and phosphates. Linkers used in the previous ADC platform are also included if they can be hydrolyzed in the said ocular environment. These include hydrazone, disulfide, dipeptide, beta-glucuronide (Kim and Kim 2015, Peters and Brown 2015). In addition, the linker can be small molecule polymer conjugate, such as PEG and small molecule complex.

The ADS compound can be delivered via intravitreal injection, subconjunctival injection, subtenon, topical eye drop or other ways to deliver to either the back or front of the eye for treating various ocular neovascular diseases. The release rate of the small molecule agent could be determined based on the course of disease progression.

The advantages of this invention are: 1) It can avoid the side effects of oral small molecule multi-kinase inhibitors by using a local delivery route; 2) The biologic drug not only has its own efficacy against the neovascular disease but also acts as a carrier of small molecule agents to enhance its original effects and to modulate additional targets; 3) Cleavable linker can be designed to be hydrolyzed near the target tissue such as in vitreous humor, aqueous humor, sub-tenon, cornea, conjunctiva or choroid, retina within several hours to several months to prolong treatment duration. This novel concept will also solve the difficulty of formulating a small molecule for posterior ocular delivery, such as intravitreal delivery; 4) The invention will allow selection of any combinations of biologic agents and small molecule agents that had proven efficacy in the clinic by themselves to achieve synergistic effects, thus enhancing the likelihood of success. Such ADS molecules will enhance the effectiveness by targeting multiple pathogenic pathways of ocular neovascular diseases. In addition to the primary target disease of wet AMD, the invention will also be useful for other angiogenesis and fibrosis indications, for example: age-related macular degeneration (AMD), choroidal neovascularization (CNV), choroidal neovascular membrane (CNVM), cystoid macular edema (CME), epi-retinal membrane (ERM) and macular hole, myopia-associated choroidal neovascularisation, vascular streaks, retinal detachment, diabetic retinopathy, diabetic macular edema (DME), atrophic changes of the retinal pigment epithelium (RPE), hypertrophic changes of the retinal pigment epithelium (RPE), retinal vein occlusion, choroidal retinal vein occlusion, macular edema, macular edema due to retinal vein occlusion, retinitis pigmentosa, Stargardt's disease, glaucoma, inflammatory conditions, cataract, regractory anomalies, ceratoconus, retinopathy of prematurity, subretinal edema and intraretinal edema, angiogenesis in the front of the eye, corneal angiogenesis following keratitis, corneal transplanation or keratoplasty, corneal angiogenesis due to hypoxia and pterygium.

In summary, the ADS technology uses a biologic drug-small molecule linked via a linker to treat ocular neovascular diseases such as wet AMD. The biologic drug can include any anti-angiogenesis antibodies (exemplified by bevacizumab, ranibizumab), fusion proteins (exemplified by aflibercept and conbercept) and any other anti-VEGF or PDGF proteins (exemplified by anti-PDGF Fovista, anti-VEGF or -PDGF Darpin). The antibody can be PEGylated. The small molecule agent can include any kinase inhibitors that inhibit both VEGFR and PDGFR (exemplified by sunitinib, nintedanib). The linkers in the disclosure include all bonds that allow cleavage in ocular tissues or fluids such as vitreous humor. Such an ADS molecule will target at least two key pathogenic pathways (e.g., VEGF and PDGF) of ocular neovascular diseases. In addition to ocular diseases, other indications that can be treated with local drug delivery are also included in this application. Examples are dermatological and joint diseases such as psoriasis and arthritis. Inflammation is a major pathogenic factor in psoriasis and arthritis and many biologics and small molecule agents have been developed to treat these diseases. These drugs modulate various targets involved in inflammation. Although most these current treatments depend on systemic drug delivery, local drug administration can also work (Jones et al 2016; Aalbers et al 2015; Tsianakas et al 2016). The ADS technology proposed here can also improve the treatment of these indications by introducing synergistic therapeutic effects.

INVENTIVE EXAMPLES

As an example, bevacizumab is linked to nintedanib by a linker that hydrolyzes in vitreous humor with a half-life of 3-4 days. In this ADS, bevacizumab retains its VEGF blocking activity. Upon intravitreal injection to the vitreous humor, nintedanib will be slowly released from the ADS compound and maintain an effective concentration before the parent ADS compound is cleared. The ADS will induce regression of neovasculariztion and improve the treatment effectiveness due to the synergism resulting from the blocking of multiple pathogenic pathways by both bevacizumab and nintedanib. Bevacizumab blocks VEGF-A. Nintedanib blocks all three VEGFRs, thus achieving more effective inhibition of the VEGF signaling pathway. Nintedanib also inhibits PDGFRs and FGFRs to provide additional therapeutic benefits for wet AMD.

REFERENCES

Csaky K G, Dugel P U, Pierce A J, Fries M A, Kelly D S, Danis R P, Wurzelmann J I, Xu C F, Hossain M, Trivedi T. Clinical evaluation of pazopanib eye drops versus ranibizumab intravitreal injections in subjects with neovascular age-related macular degeneration. Ophthalmology. 2015; 122(3):579-88.

Jo N, Mailhos C, Ju M, Cheung E, Bradley J, Nishijima K, Robinson G S, Adamis A P, and Shima D T. Inhibition of Platelet-Derived Growth Factor B Signaling Enhances the Efficacy of Anti-Vascular Endothelial Growth Factor Therapy in Multiple Models of Ocular Neovascularization. Am J Path. 2006;168: 2037-53.

Kim E G and Kim K M. Strategies and Advancement in Antibody-Drug Conjugate Optimization for Targeted Cancer Therapeutics. Biomol Ther. 2015; 23(6): 493-509.

Kudelka M R, Grossniklaus H E, Mandell K J. Emergence of Dual VEGF and PDGF Antagonists in the Treatment of Exudative Age-Related Macular Degeneration. Expert Rev Ophthalmol. 2013;8(5): 475-484.

Martin D F, Maguire M G, Ying G S et al. Ranibizumab and bevacizumab for neovascular age-related macular degeneration. The CATT Research Group. N. Engl. J. Med. 2011;364(20): 1897-1908.

Peters C. and Brown S. Antibody—drug conjugates as novel anti-cancer Chemotherapeutics. Bioscience Reports. 2015;35: e00225.

Rosenfeld P J, Brown D M, Heier J S et al. Ranibizumab for neovascular age-related macular degeneration. N. Engl. J. Med. 2006;355(14): 1419-1431.

Stewart M W, Grippon S, Kirkpatrick P. Aflibercept. Nat. Rev. Drug Discov. 2012;11(4): 269-270.

| Abbreviation Table | |
|---|---|
| Abbreviation | Full term |
| ADS | Antibody-Drug Synergism |
| AMD | Aage-related macular degeneration |
| FGF | Fibroblast growth factor |
| FGFR | Fibroblast growth factor receptor |
| PDGF | Platelet-derived growth factor |
| PDGFR | Platelet-derived growth factor receptor |
| VEGF | Vascular endothelial growth factor |
| VEGFR | Vascular endothelial growth factor receptor |

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound comprising:
   an antibody, the antibody being bevacizumab;
   a small molecule agent, the small molecule agent being nintedanib; and
   a linker that links the antibody to the small molecule agent, the linker being hydrolyzable in vitreous humor.

2. The compound of claim 1, wherein the antibody is PEGylated.

3. The compound of claim 1, wherein the linker is an ester, a carbonate, a carbamate, an ether, an amide, an imine, a phosphate, or a hydrozone bond.

4. The compound of claim 1, wherein the compound is a dry powder for rehydration before use, a gel, or an implant.

* * * * *